United States Patent
Kadir et al.

(10) Patent No.: US 9,563,947 B2
(45) Date of Patent: Feb. 7, 2017

(54) MEASUREMENT SYSTEM FOR MEDICAL IMAGES

(75) Inventors: Timor Kadir, Oxford (GB); Mark Gooding, Oxford (GB)

(73) Assignee: Mirada Medical Limited, Oxford (GB)

( * ) Notice: Subject to any disclaimer, the term of this patent is extended or adjusted under 35 U.S.C. 154(b) by 35 days.

(21) Appl. No.: 14/110,011

(22) PCT Filed: Apr. 3, 2012

(86) PCT No.: PCT/EP2012/056098
§ 371 (c)(1),
(2), (4) Date: Oct. 4, 2013

(87) PCT Pub. No.: WO2012/136669
PCT Pub. Date: Oct. 11, 2012

(65) Prior Publication Data
US 2014/0029815 A1    Jan. 30, 2014

(30) Foreign Application Priority Data
Apr. 5, 2011    (GB) .................................. 1105725.4

(51) Int. Cl.
*G06K 9/00*    (2006.01)
*G06T 7/00*    (2006.01)
(Continued)

(52) U.S. Cl.
CPC ............. *G06T 7/0012* (2013.01); *A61B 6/463* (2013.01); *A61B 6/467* (2013.01); *A61B 8/461* (2013.01);
(Continued)

(58) Field of Classification Search
CPC .. G06T 7/60; G06T 2207/20092; G06T 7/602; G06K 2009/366; G06K 9/4638
See application file for complete search history.

(56) References Cited

U.S. PATENT DOCUMENTS 7,539,332 B1 *    5/2009    Al-Dayeh et al. ............. 382/128
7,856,132 B2 *   12/2010    Nijlunsing et al. ........... 382/131
(Continued)

FOREIGN PATENT DOCUMENTS

JP    04358290 A    4/1991
JP    02921078 B2    7/1999
(Continued)

OTHER PUBLICATIONS

PCT Search Report and Written Opinion for PCT/EP2012/056098, completed Aug. 21, 2012.
(Continued)

*Primary Examiner* — Bhavesh Mehta
*Assistant Examiner* — Ian Lemieux
(74) *Attorney, Agent, or Firm* — Optimus Patents US, LLC

(57) ABSTRACT

A method of measuring a parameter of a structure (212) on a medical image (200) comprises a measurement tool (220) displayed on a slice of the image. An automated point detection function identifies a point within at least one region (250) of the image that optimizes the placement of the respective end of the measurement tool (220). The region may be 2-d or 3-d. The identified point(s) are then used to calculate the parameter, which may be distance, angle, area or volume. The measurement tool (320) may move to the identified points (330, 340). A system (2000), computer program and computer-readable medium are also provided. The invention may make the measurement of tumors, and measurements of the spacing within or between various structures on a medical image, more accurate and/or more consistent.

27 Claims, 20 Drawing Sheets

(51) Int. Cl.
*A61B 6/00* (2006.01)
*G06T 19/00* (2011.01)
*G06T 7/60* (2006.01)
*A61B 8/00* (2006.01)

(52) U.S. Cl.
CPC ............ *A61B 8/469* (2013.01); *G06T 7/0051* (2013.01); *G06T 7/60* (2013.01); *G06T 19/00* (2013.01); *A61B 8/467* (2013.01); *G06T 2207/20101* (2013.01); *G06T 2207/30096* (2013.01); *G06T 2210/41* (2013.01)

(56) References Cited

U.S. PATENT DOCUMENTS

| 8,036,436 | B2* | 10/2011 | Geiger | A61B 8/13 |
| | | | | 382/128 |
| 2006/0171580 | A1* | 8/2006 | Blanford | G01N 21/8806 |
| | | | | 382/141 |
| 2008/0228061 | A1* | 9/2008 | Habets | 600/407 |
| 2009/0180677 | A1* | 7/2009 | Li et al. | 382/131 |
| 2010/0215245 | A1* | 8/2010 | Olivan Bescos | 382/133 |

FOREIGN PATENT DOCUMENTS

| WO | 2005055008 | A2 | 6/2005 |
| WO | 2005071527 | A2 | 8/2005 |

OTHER PUBLICATIONS

IPO Search Report and Written Opinion for GB1105725.4, completed Jul. 13, 2011.

* cited by examiner

MEASUREMENT SYSTEM FOR MEDICAL IMAGES

FIELD OF THE INVENTION

The present invention concerns the measurement of structures within images, the images being generated in the field of medicine.

BACKGROUND OF THE INVENTION

A variety of technologies can be used to provide medical images. Typical modern sources of medical images are ultrasound scans, CT scans and MRI scans.

Most medical imaging involves images of humans. However, images may also be obtained of non-human animals, particularly as part of medical research projects. Medical images need to be read, analysed and reviewed by specialists.

Medical images may include information about a wide variety of anatomical features, structures, spaces and distances. For example, an image may show various types of healthy tissue, such as bone and/or organs, within the body. An image may also show abnormal tissues, such as tumours, cysts, swollen glands or other lesions. The word 'tumour' should henceforth be construed to include other types of abnormal tissues.

It is often necessary to estimate the size and volume of anatomical structures that are shown in medical images. The size of healthy tissue may be determined in order, for example, to measure growth in children.

These estimates may also serve, for example, to monitor the growth of abnormal tissue. Both the size of abnormal tissue, and the spacing between abnormal tissue and healthier tissue, may be of interest.

Here a 'structure' should be interpreted very broadly, and might include:
(i) A single entity, such as an organ, bone or tumour.
(ii) A group of essentially separate objects, such as ribs in a rib cage, or two separate tumours visible on one image.
(iii) A gap bordered by two or more objects or edges, such as the spacing between a tumour and the surface of a body, or between a tumour and a nearby organ.

Henceforth, a 'structure' that may be measured on an image may in fact be a single entity, or even a spacing between two different entities.

One prior art example where measurements are necessary is in the reading of images from cancer patients. Measurements of the principal dimensions of any suspected tumours are typically required for diagnosis and staging of disease. These measurements are also required for assessing the efficacy of any administered treatment.

In other fields of medicine, it may be necessary to obtain estimates of:
(i) The size or volume of normal anatomy, e.g. organs; or
(ii) Distances or angles between anatomical structures.

Much existing medical practice was developed for non-digital 2-d images, such as X-Ray films. Radiologists may obtain measurements directly from the hard copy of the image, using callipers or a ruler.

However, medical images are increasingly obtained and manipulated in digital format. In digital Radiology, either 2-d ('2-d') or 3-d ('3-d') images may be available. If the original image was only 2-d, then a user views a 2-d representation of that image.

A 3-d image from a scan typically includes a large volume of data points. Henceforth, the word 'image' describes the collection of all these data points. Normally therefore an 'image' will mean a 3-d image, but some embodiments of the present invention are applicable to 2-d images, such as those often obtained from ultrasound scans.

A user will normally view only one individual 2 dimensional 'slice' through the 3-d image. An image slice from a 3-d image is simply a 2-d representation, consisting of those data points that lie on a particular 2-d plane through the 3-d image. A typical 3-d image, such as one from an MRI scan, will have a matrix of regularly spaced data points. As a non-limiting example, the MRI-scan may have data points whose centres are spaced by 1 millimeter in the x- and y-directions across any plane of the scan. Consecutive planes may, for example, be parallel and separated by 7 millimeters.

Although it is usual for data points to be in the plane of a viewed image slice, it is possible that the points only lie near to the plane of the slice, for example when an 'off-axis' viewing angle has been selected.

Medical imaging workstations commonly provide tools for obtaining the required measurements directly from the displayed image slices.

Examples of the tools available on medical imaging workstations are digital callipers or a digital ruler. When working with such tools, the user is typically required to select and then click onto two reference points on the image slice. The workstation then calculates the real-world distance between the two reference points, and reports the result in cm or mm. Here 'real-world' means the distance on the object that was scanned, rather than the distance across the screen.

FIG. 1 generally illustrates a conventional ruler, available on current medical imaging workstations.

In FIG. 1, reference 100 indicates a medical image slice. Image slice 100 is displayed on a screen 105, which may be part of a medical imaging workstation.

Reference 110 indicates schematically the outer edge of a portion of medical image slice 100, i.e. of the object that was scanned. Reference 110 may, for example, indicate the outer edge of a torso.

Reference 112 shows a structure, also in cross-sectional view, that is located on medical image slice 100. Structure 112 might be a tumour, but might instead be an organ. Only portions of the tumour or organ that lie in the plane of the image slice 100 will be visible. Other portions that lie in neighbouring image slices, will not be visible on slice 100.

Reference 120 shows a linear ruler, which is unidirectional. A user has aligned linear ruler 120 between points 130 and 140 on structure 112, having selected these points as being of significance. The user has identified points 130 and 140 as being the end points of the longest axis or diameter of structure 112.

The linear ruler 120 then provides a readout of the distance between points 130 and 140. The readout is shown as 28 mm on FIG. 1. The numerical value of the measurement may be superimposed on the displayed slice 100, adjacent to the linear ruler 120, as shown in FIG. 1. Alternatively or in addition, the measurement may be displayed elsewhere on the screen, or recorded elsewhere, such as in a table accessible by viewing another screen.

Two examples of alternative workstation tools are:
(i) A virtual ruler. This tool requires the user to click, and sometimes also drag, either end of the ruler to the appropriate locations on the medical image.
(ii) A virtual protractor. This tool requires the user to click and drag either end of a pair of 'hinged' lines to the appropriate locations on the medical image. The workstation then reports the angular measurement.

Such tools as the virtual ruler and virtual protractor almost exclusively operate in 2D images, or in 2D slices extracted from 3D images.

The types of measurement of interest on a medical image may include:
(i) The largest diameter or length, in the plane of acquisition of the image. This diameter is known as the 'long axis'.
(ii) The largest diameter or length, perpendicular to the long axis. This diameter is known as the 'short axis'.
(iii) The volume.
(iv) One or more other distances.
(v) One or more angles.

Within the field of oncology, it is common clinical practice to measure the size of suspected tumours. This size measurement is made using the long and short axes, in a particular plane. Here 'plane' is important. It means a particular direction, in which the slice must be taken.

Two standard methods are in widespread use for the evaluation of treatment response in oncology. One, referred to as the 'WHO' standard, requires that both the long and short axes of each tumour be measured. The other method is the 'RECIST' standard. The 'RECIST' standard requires only measurement of the long axis of each tumour. In a recent version, RECIST 1.1, the measurement of the short axis is used for assessing lymph-nodes, instead of the measurement of the long axis.

The digital ruler and calliper tools provided on medical imaging workstations require the user to carry out either two or three manual steps. These steps are the following sequence, with at least step 1 and one of steps 2 or 3 being necessary:

Step 1: Manually select the slice, i.e. the particular 2-d image from amongst all the image data or images that were taken of the structure. Normally, the 2-d image slice that is selected will be the one that appears to have the longest tumour dimension.

Step 2: On screen, define the start and finish of the long axis measurement, and use a ruler or digital callipers to make the measurement.

Step 3: On screen, define the start and finish of the short axis measurement, and use a ruler or digital callipers to make the measurement.

The known prior art has a number of disadvantages regarding the accuracy, reproducibility and optimality of measurement tool control and placement. Some of these disadvantages are as follows:
(i) The user must judge the appropriate locations in the slice at which to specify the control points of the measurement tool, in order to obtain the required measurement. For some features, this is relatively straightforward. However, for other features, the true boundary may be unclear. The result is variability in the measurements obtained, for example by different users, even when those users are experienced.
(ii) The interface for the interaction required, typically a computer mouse, may be hard to control precisely, leading to inaccurate placement or variability even between the same user making a measurement twice.
(iii) The screen resolution at which the slice and interactive tool location are displayed may affect the accuracy to which the control point can be placed.
(iv) For some types of measurement, such as the long axis and short axis, the approximate axis placement and direction may be easily discernable to the user. However, the selection of optimal image slice, axis direction and control point position placement may be significantly harder. This may lead to errors from arbitrary choice of placement. It may also lead to laborious measurements, when repeat measurements are undertaken for optimisation.
(v) For measurements of the same object across a series of images, the measurements usually require consistency. This requirement may relate, for example, to slice orientation, slice choice, the definition of the object boundary, or axis direction. Although clinical users will attempt to be consistent, accurate and reproducible placement of control points to enforce such consistency across images in a series is difficult and error prone.

Increasingly, volumetric measurements are becoming of interest in medical imaging. Here it is necessary either to manually delineate the tumour or other structure, or to use automated or semi-automated algorithms. Examples of such algorithms are known from the following prior art publications:
(i) Marie-Pierre Jolly and Leo Grady, "3D General Lesion Segmentation in CT", Proc. of ISBI 2008, Paris, France, May 14-17 2008. pp. 796-799.
(ii) Radiology reference: Zhao B, Reeves A P, Yankelevitz D, Henschke C I. Three-dimensional multi-criterion automatic segmentation of pulmonary nodules of helical CT images. Opt Eng 1999; 38:1340-1347.

Automated and semi-automated volumetric approaches attempt to overcome the limitations of ruler based approaches. They achieve this by enabling the user to define a 2-d or 3-d segmentation of the object requiring measurement, for example a tumour. The volume and maximum dimensions can then be derived from such segmentations.

Where a tumour has clear well-defined boundaries, such automated and semi-automated volumetric techniques can be useful. However, in many cases, medical images exhibit poorly defined boundaries. In addition, tumours are often within or adjacent to tissue of a similar radiological appearance. It is therefore difficult to distinguish tumour tissue from other tissues present in the same region of the image.

In such cases, existing tools for automated or semi-automated volumetric techniques either completely fail, or require a significant degree of user intervention to produce a successful result. This can be unsatisfactory, because in many cases the user is compelled to produce an accurate 2-d or 3-d segmentation, when all that was required was a simple 2-d linear measurement.

There is a need for a simple, fast, accurate and reproducible method for the placement of control points of measurement tools. This need arises when determining measurements of an object, such as healthy tissue, or a tumour or other structure, from a medical image.

Consistency of control point placement for measurements over a series of images is also important. This need applies to a series of images that are obtained by one technique at the same time, and to such a series obtained at different times. It also applies to multiple images obtained by different techniques, such as MRI and CT scans, whether during an investigation at one point in time or on different occasions.

STATEMENT OF INVENTION

A first aspect of the invention comprises a method in accordance with appended claim 1.

A second aspect of the invention comprises a system in accordance with appended claim 26.

A third aspect of the invention comprises a medical imaging workstation in accordance with appended claim 27.

A fourth aspect of the invention comprises a computer program in accordance with appended claim 28.

A fifth aspect of the invention comprises a computer-readable medium in accordance with appended claim 29.

The method and system of the invention enable the measurement of a parameter of a structure on a medical image, based on features of interest. The parameter may, for example, be distance, angle, area or volume. The method and system of the invention optimise the placement of the respective ends of a measurement tool, displayed on an image slice.

The invention may perform measurements between 'control points' that lie within a single displayed slice of a larger medical image.

However, the invention may instead locate and make a measurement from one or more control points that do not lie in the displayed slice. If the invention selects a control point that lies in a slice of the image that was not originally displayed, then a new slice may be displayed that does include all the control points. Thus the invention may lead to the display of a new slice of a medical image that shows the most important dimension of a structure of interest, even if the originally displayed slice was in a different plane.

The invention may increase the accuracy and/or the repeatability, i.e. consistency, of measurements of tumours, and measurements of the spacing within or between various structures on a medical image.

The system of the invention may be included in a medical imaging workstation. The method of the invention may be applied to multiple images. A computer program and computer readable medium are also provided.

DESCRIPTION OF PREFERRED EMBODIMENTS

The invention provides a method of measuring a parameter of a structure on a medical image. Such images are obtained through a variety of digital scanning processes, such as ultrasound scans, CT scans and MRI scans.

Tumours or anatomical features are examples of structures for which measurements may be sought. A 'structure' might include a single entity, a group of essentially separate objects, or a gap bordered by two or more objects or edges.

The medical image is displayed as a 'soft copy'. Normally, the image will have been obtained by a 3-d scan. For an image that has been captured in 3-d, the display will be of a particular 'slice' through the 3-d image. If only a 2-d image was captured, that 2-d image is displayed. Henceforth, reference will be made to the image 'slice', to cover both these possibilities.

A measurement tool comprising at least two ends is displayed on the image slice. When the measurement tool is visible on the displayed image slice, a user of the system can move the ends of the measurement tool to positions in proximity to corresponding features of interest. The features of interest are part of the structure. Alternatively, the measurement tool may only appear on the display when the user has already selected locations for the ends of the tool, close to the features of interest. A computer mouse, tracker ball or touch screen may be used to move the ends of the measurement tool, or to select the locations where the ends of the tool are to appear.

Figure 2:
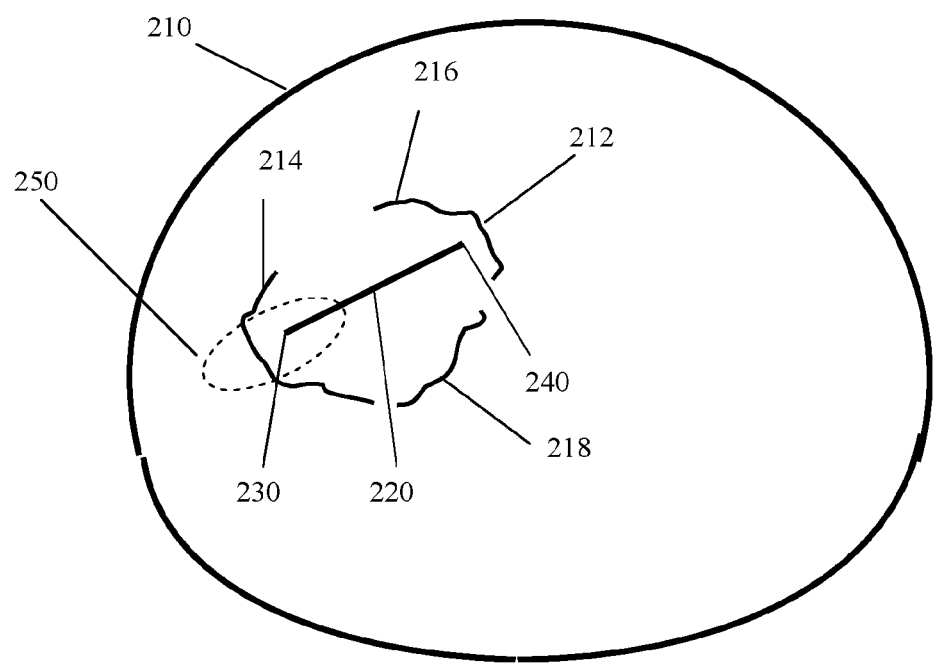
FIG. 2 shows a view of a measurement tool in accordance with an embodiment of the invention.
Figure 3:
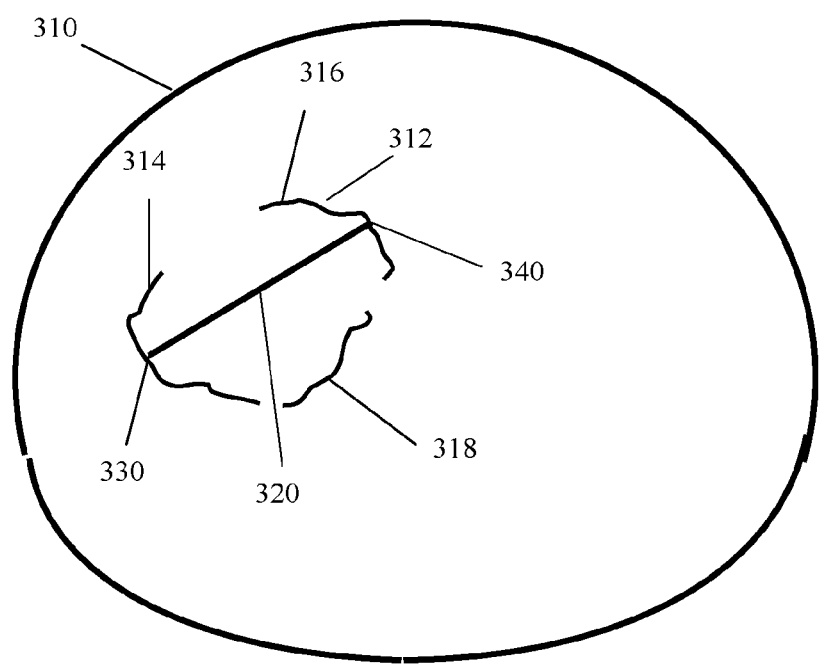
FIG. 3 shows a subsequent view of the measurement tool of FIG. 2.
Figure 4:
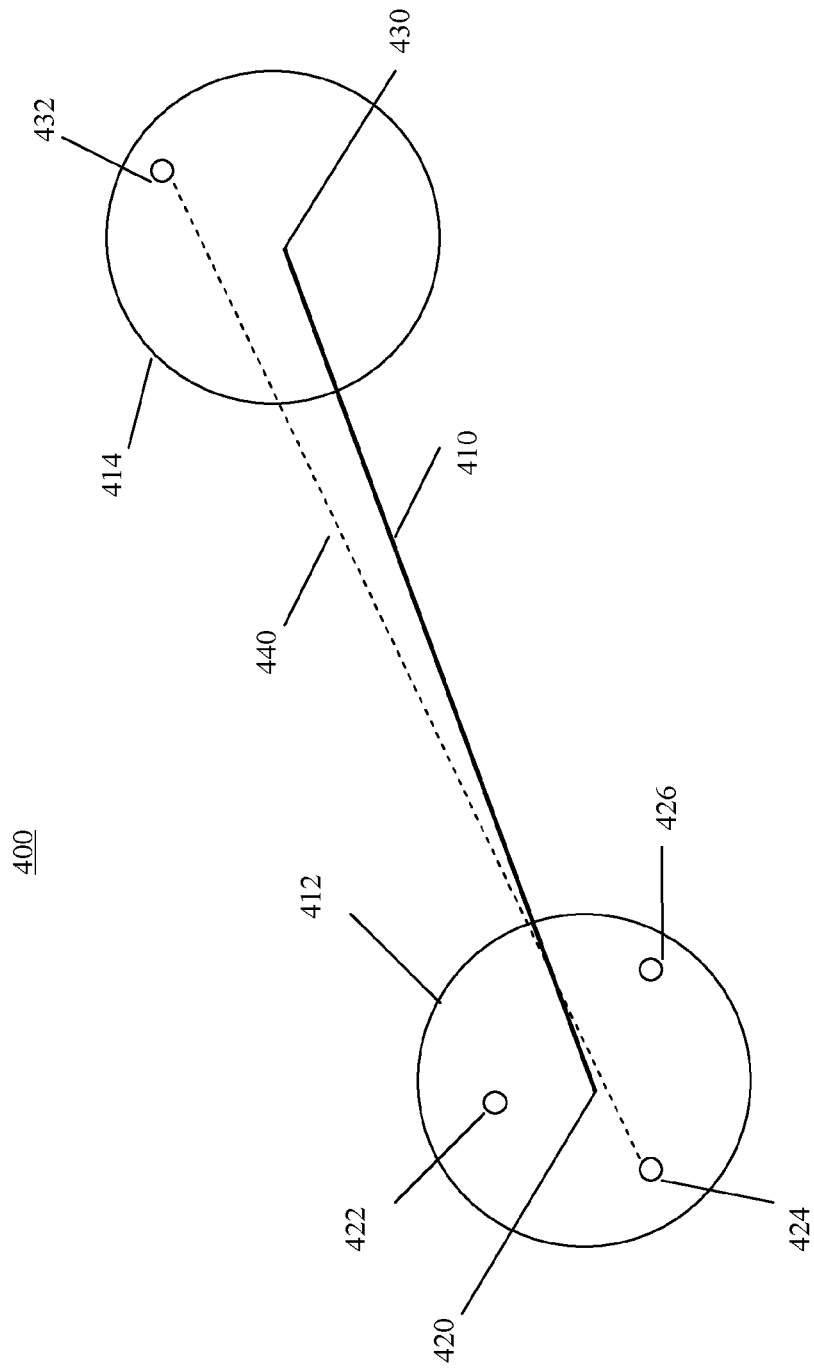
FIG. 4 shows an embodiment of the invention that provides a sub-set of one or more candidate features of interest.

2-d Implementations of the Invention (FIGS. 2-4)

Figure 1:
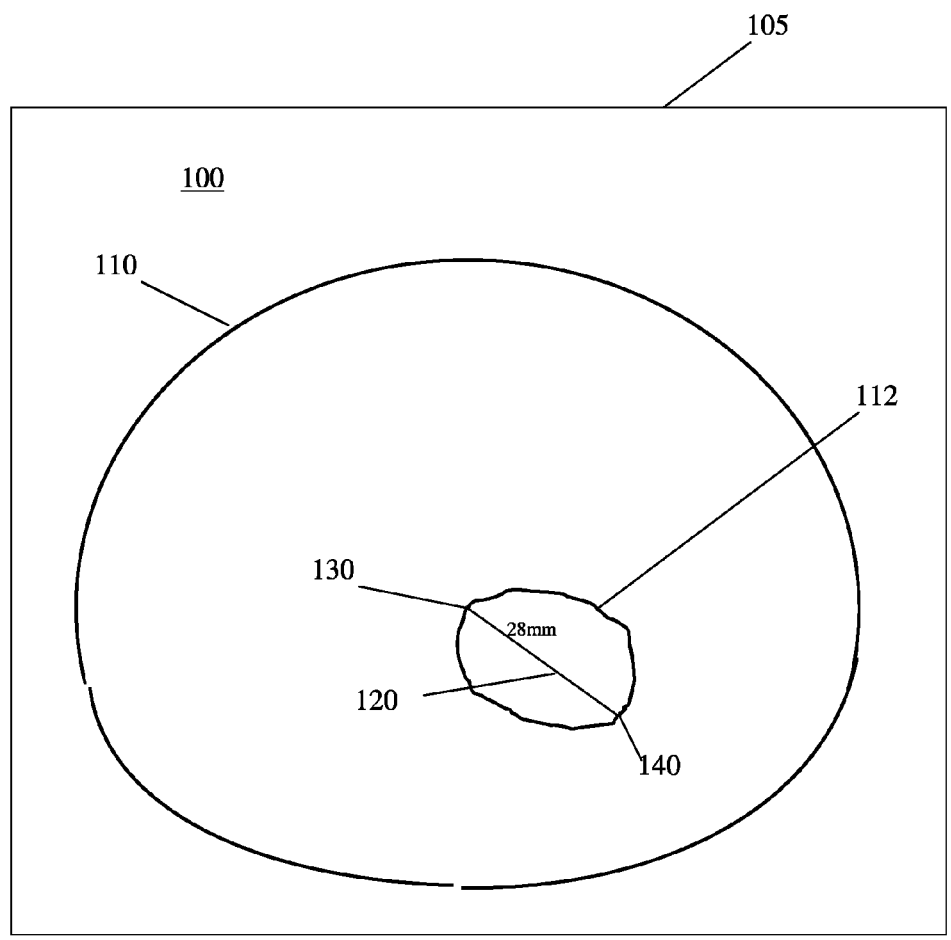
FIG. 1 shows a measurement tool in accordance with the prior art.

FIG. 2 shows an embodiment of the invention. An image slice 200 is displayed on a screen. The screen shown as reference 105 in FIG. 1 has been omitted from FIG. 2 and subsequent FIGS. 3-15.

Reference 210 indicates the perimeter of a part of the image slice 200. If the image slice 200 shows a slice through a body, then reference 210 may, for example, show the perimeter of a torso.

A measurement tool 220 is displayed on the image slice. Measurement tool 220 has first end 230 and second end 240.

Image slice 200 also includes a structure generally indicated by reference 212. Reference 212 in fact indicates only one part of a generally irregularly shaped structure, which is visible on image slice 200. The three parts of the structure 212 visible on image slice 200 are first part 214, second part 216 and third part 218.

Structure 212 may in reality take various forms, depending on its nature and the resolution of the imaging system used to obtain the medical image. For example, structure 212 may be a well defined and continuous structure such as that shown as 112 on FIG. 1, or may alternatively be barely visible at all. Structure 212 shown on FIG. 2 is an example between these extremes.

First end 230 of measurement tool 220 is shown in proximity to first part 214. First part 214 constitutes or includes a first feature of interest. Second end 240 of measurement tool 220 is shown in proximity to second part 216. Second part 216 constitutes or includes a second feature of interest.

The locations of the first end 230 and second end 240 may be chosen by a user, who is interested in obtaining a measurement of a parameter of structure 212. The parameter of interest may, for example, be a length. That length may be the length of the long axis of structure 212. However, measurement tool 220 may provide a measurement that is useful in calculating an area or a volume.

The locations of first end 230 and second end 240 will only approximate to the locations of the corresponding parts 214 and 216 of structure 212. The locations of first end 230 and second end 240 act as initial 'control points', to which further steps of the method of the invention are applied.

The method of the invention involves applying an automated point detection function to at least one region of interest of the medical image. Henceforth this region of interest is referred to as a 'region'.

In the most usual implementation of the invention, each region comprises one of the ends of the measurement tool. So, when viewed on the displayed image slice, a region would have one of the measurement tool's ends within its perimeter.

However, the invention, in its broadest sense, requires that each region have a known spatial relationship to one of the ends of the measurement tool. So the invention can also be implemented by defining a region that does not include either end of the measurement tool within its perimeter. Instead, a region would be defined at some fixed or variable distance away from the end of the measurement tool. The remainder of this description focuses on examples where each region does include one end of the measurement tool.

For the measurement tool shown in FIG. 2, there are two ends 230 and 240. The point detection function may therefore be applied twice, i.e. in two regions, each region encompassing one end of the measurement tool. However, the measurement tool may have more than two ends, and the automated point detection function may be applied to one or more ends.

An example of a region to which the automated point detection function is applied is generally shown by reference 250 in FIG. 2. Region 250 encloses first end 230 of measurement tool 220, and is shown as a dotted oval. The location of region 250 is determined by the location and orientation of first end 230 of measurement tool 220.

The automated point detection function acts to identify a selected point within each region to which it is applied. The selected point is the point that optimises the placement of the respective end of the measurement tool.

In one embodiment, the automated point detection function identifies the point within the region that has the highest likelihood of being the feature of interest. The point having the highest likelihood of being the feature of interest is then selected as the selected point. The parameter measurement then proceeds with one end of the measurement tool being on that selected point. This embodiment is illustrated in FIG. 3, which is described below.

In another embodiment, the automated point detection function may instead filter potential features within the region. This step of filtering results in a sub-set of one or more candidate features of interest, within the region. The automated point detection function then identifies the one candidate feature from the sub-set that optimises the output of the measurement tool. For example, if the measurement tool is measuring a length of the structure on the displayed slice of the medical image, then the automated point detection function will identify the particular candidate feature that maximises the length of the measurement tool. This particular candidate feature therefore becomes the 'selected point' for the region. This embodiment is illustrated in FIG. 4, which is described below after the discussion of FIG. 3.

FIG. 3 illustrates the embodiment of the invention in which the automated point detection function identifies the point within the region that has the highest likelihood of being the feature of interest.

FIG. 3 shows the result of applying the automated point detection function to a displayed slice of a medical image 300. Perimeter 310, first part 314, second part 316 and third part 318 of structure 312 on FIG. 3 generally correspond to the similarly number features on medical image 200 shown on FIG. 2.

The automated point detection function has identified a point 330, on first part 314 of structure 312. Point 330 is the point in region 250 shown on FIG. 2 that has the highest likelihood of being the feature of interest.

In the view shown on FIG. 3, the first end of measurement tool 320 has actually moved to point 330, which may enable a user to see more clearly where point 330 is on medical image 300. However, the first end of measurement tool 320 could stay in the location shown by point 230 in FIG. 2. In this case, another indication such as a circle, arrow or other visual marker may be used to indicate the point 330 to the user.

Point 330 provides a more accurate placement of the first end of measurement tool 320 on the first part 314 of structure 322, for the purposes of measuring a parameter, which may lead to greater accuracy and/or consistency in calculating various parameters of structure 312.

In accordance with the invention, a measurement of the parameter of structure 312 is performed, using point 330.

In the embodiment shown in FIG. 3, the second end of the measurement tool 320 has moved to a point 340 on the second part 316 of structure 312. Point 340 was identified by applying the automated point detection function to a second region, which enclosed second end 240 of measurement tool 220 on FIG. 2.

The measurement of the parameter of structure 312 may thus be performed using both points 330 and 340. However, if only point 330 is identified, and not point 340, then the parameter measurement would instead be based on point 330 and the location shown as 240 on FIG. 2. The method of the invention would provide maximum accuracy in calculating parameters of structure 312 when both points 330 and 340 can be identified.

The automated point detection function may comprise an assessment of object edge likelihood. If such an assessment is made, then the result may involve identifying the location of the point having the highest object edge likelihood, within each region. This approach may lead to a placement of one or both ends of the measurement tool 320 at a point or points that are substantially more accurate than the original locations of the first and second ends 230, 240 chosen by the user and as shown in FIG. 2.

The automated point detection function may comprise an assessment of the rate of intensity variation, the selected point being the point where the rate of intensity variation is maximum.

FIG. 4 illustrates the embodiment of the automated point detection function that:
(i) filters potential features within the region to provide a sub-set of one or more candidate features of interest; and then
(ii) identifies one candidate feature from the sub-set that optimises the output of the measurement tool.

FIG. 4 shows just the measurement tool 410 displayed on an image slice 400, without further detail of the image slice.

The automated point detection function is applied in a circular region 412 around the location at which a user has placed first end 420 of measurement tool 410. The automated point detection function identifies a subset of points 422, 424 and 426, which are candidate features.

The automated point detection function then identifies candidate feature 424 as being the candidate feature within region 412 that optimises the output of the measurement tool. In the example of FIG. 4, the measurement tool is measuring a length of the structure on the displayed slice of the medical image. Choosing candidate feature 424 maximises the length of the measurement tool, so this particular candidate feature therefore becomes the 'selected point' for the region. The measurement tool has been shown in a second location, after application of the point detection function, as reference 440. The leftmost end of the measurement tool 440 is on selected point 424.

The automated point detection function is also applied in a circular region 414 around the location at which a user has placed second end 430 of measurement tool 410. The automated point detection function identifies a subset of only one candidate feature, at point 432, which meets the selection criteria. Examples of possible selection criteria are discussed later. So point 432 becomes the 'selected point' in region 414. In its second location, measurement tool 440 has been shown with its rightmost end on selected point 432.

The result of applying the automated point detection function in regions 412 and 414 of FIG. 4 is to reposition the measurement tool to location 440, from its initial location 410. The length measurement is thereby optimised.

Each of FIGS. 1-4 above shows a single displayed slice of a medical image. In FIGS. 2-4, the automated point detection function is applied in a region 250, 412 or 414 that is a two dimensional area of the displayed slice of the medical image. The region lies in the same plane as the displayed slice of the medical image, and is a two dimensional area. So each selected point 330, 340 lies within the displayed slice of the medical image and, in the optimised placement, the ends of the measurement tool lie within the plane of the displayed slice of the medical image.

As a result, moving at least one end of the measurement tool to the selected point on the displayed slice of the medical image results in the measurement tool remaining in the single displayed slice of a medical image.

Figure 5:
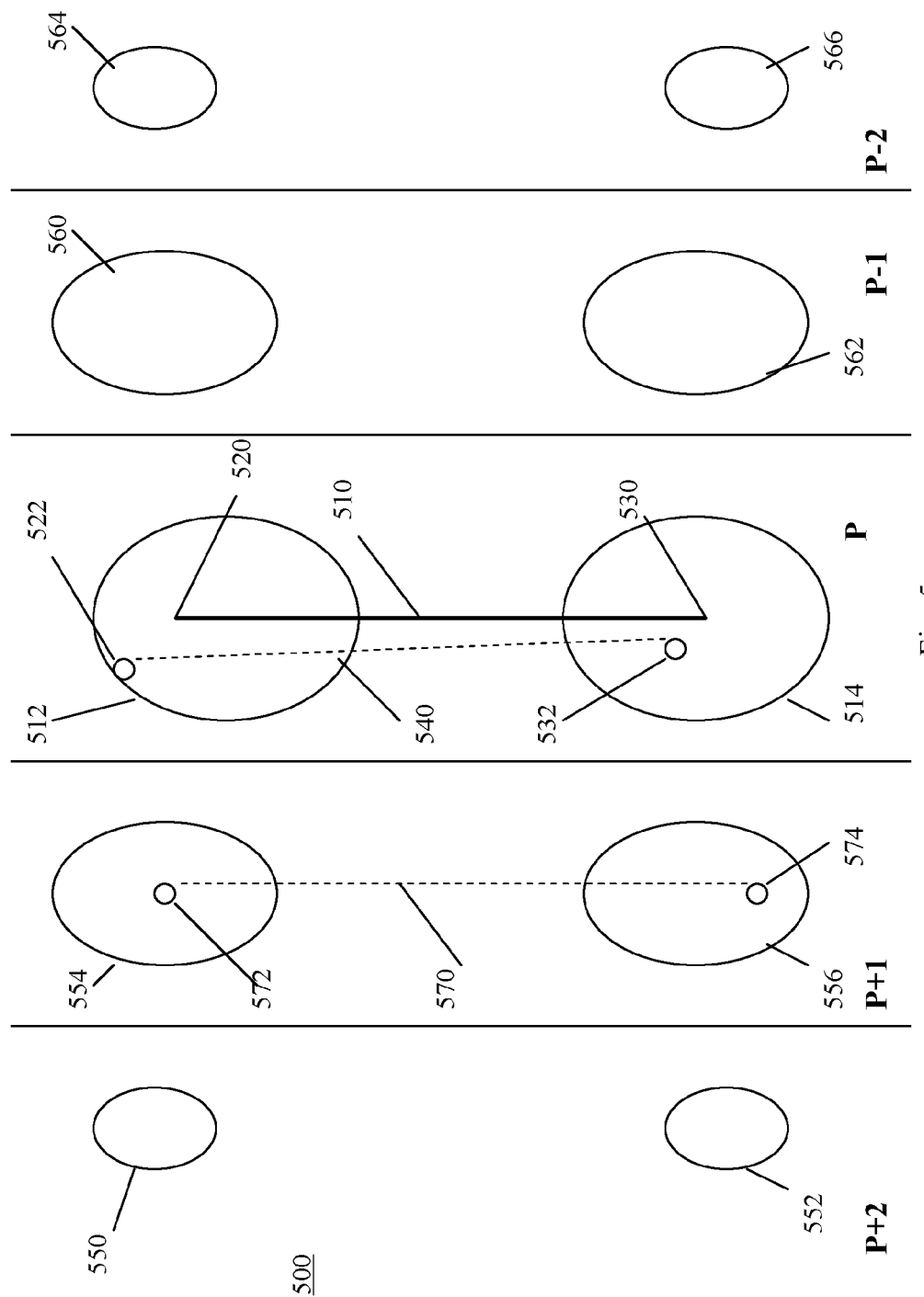
FIG. 5 shows plan views of five successive slices of a medical image, to which the invention may be applied.

3-d Implementation of the Invention (FIG. 5)

A further embodiment of the invention may utilise to its advantage the 3-d nature of the medical image data. A 3-d image includes data points that lie in slices that are above and/or below the displayed slice of the medical image. In the further embodiment, the automated point detection function may be applied in a 3-d region, rather than the 2-d region 250, 412, 414 shown in FIGS. 2 and 4. This further embodiment may be implemented either to select the single best point, or a sub-set of one or more candidate features of interest.

In this further embodiment, the automated point detection function is still applied to regions of a medical image that surround the ends of a measurement tool, or have a fixed spatial relationship to the ends. However, each region encompasses a 3-d volume of the medical image. Each region comprises part of the displayed slice of the medical image, and part of at least one other slice of the medical image. These regions will be referred to henceforth as '3-d regions'.

For each 3-d region, the automated point detection function identifies a selected point within one of the image slices that optimises the placement of the respective end of the measurement tool. As a result, one or more ends of the measurement tool may need to be placed within other slices of the medical image than the displayed slice.

One advantage of such an approach is that it allows placement of the measurement tool in a plane that differs from the plane of the originally displayed image slice. So, for example, the longest dimension of a structure may be identified and measured, even if that dimension does not lie in the plane of the single image slice that was originally chosen for display by the user.

At least one end of the measurement tool may be moved to the point selected by the automated point detection function. If at least one end of the measurement tool does not lie within the displayed slice, then this may also involve displaying a new slice of the medical image. The new slice comprises the ends of the measurement tool, but may not be parallel to the image slice that was originally chosen for display by the user.

FIG. 5 shows the invention applied to a 3-d region of the medical image.

In order to understand FIG. 5, it is useful to consider the two dimensional region 250 shown in FIG. 2. A three dimensional region around the end of the measurement tool 220 in FIG. 2 might be created by rotating the oval region 250 about the axis of measurement tool 220. This would create an ovoid 3-d region, i.e. shaped like an American football or a rugby ball. Such a 3-d region might have its widest plane in the plane of the displayed slice of the medical image. The 3-d region would intersect successively smaller areas of other slices of the medical image, which lay above or below the displayed slice.

FIG. 5 shows views of five successive slices of a medical image. Four vertical lines have been included on FIG. 5 to divide up the five successive slices.

The slice labelled 'P' in the centre of FIG. 5 is the initially displayed slice of the medical image. Slice 'P+1' lies immediately above slice 'P', and slice 'P+2' lies above slice 'P+1'. Slice 'P−1' lies below slice 'P', and slice 'P−2' lies below slice 'P−1'. Only slice 'P' is visible on the display screen of the medical imaging workstation. However, the data for the other four slices is held as part of the medical image.

Slice P includes a measurement tool 510. Region 512 surrounds end 520 of measurement tool 510. Region 514 surrounds end 530 of measurement tool 510.

Regions 512 and 514 are both 3-d regions. Region 554 represents the intersection of region 512 with plane 'P+1', and region 556 represents the intersection of region 514 with plane 'P+1'.

Region 550 represents the intersection of region 512 with plane 'P+2', and region 552 represents the intersection of region 514 with plane 'P+2'.

Region 560 represents the intersection of region 512 with plane 'P−1', and region 562 represents the intersection of region 514 with plane 'P−1'. Region 564 represents the intersection of region 512 with plane 'P−2', and region 566 represents the intersection of region 514 with plane 'P−2'.

When the automated point detection function is applied to the 3-d region represented by references 512, 550, 554, 560 and 564, it identifies two candidate features of interest, at points 522 and 572. Point 522 lies in plane P, and point 572 lies in plane P+1, and these two features make up the sub-set of candidate features for the region.

Similarly, when the automated point detection function is applied to the 3-d region represented by references 514, 552, 556, 562 and 566, it identifies two candidate features of interest, at points 532 and 574. Point 532 lies in plane P, and point 574 lies in plane P+1, and these two features make up the sub-set of candidate features for the region.

If the measurement tool is constrained to lie within plane P, then dashed line 540 represents the optimised position of the measurement tool. Here the length of the measurement tool is being maximised, and the measurement tool joins points 522 and 532.

If the measurement tool is, instead, only constrained to lie in any plane parallel to plane P, then dashed line 570 in plane P+1 represents the optimised position of the measurement tool. The measurement tool joins points 572 and 574.

If, instead, the measurement tool can lie in any plane, then the measurement tool's length is optimised when it connects point 522 in plane P to point 574 in plane P+1.

The view displayed to the user may then be changed from that shown in FIG. 5 as plane P, to that shown as view 600 in FIG. 6, described below.

As an alternative to the selection process described above that leads to the sets of candidate features 522,532,572 and 574, the embodiment of FIG. 5 may result only in the selection of a single point in each of regions 512 and 514 that has the highest likelihood of being the feature of interest. These may turn out to be points 532 and 572, for example. In a further alternative, the point detection function may be applied to only one of regions 512 and 514.

Figure 6:
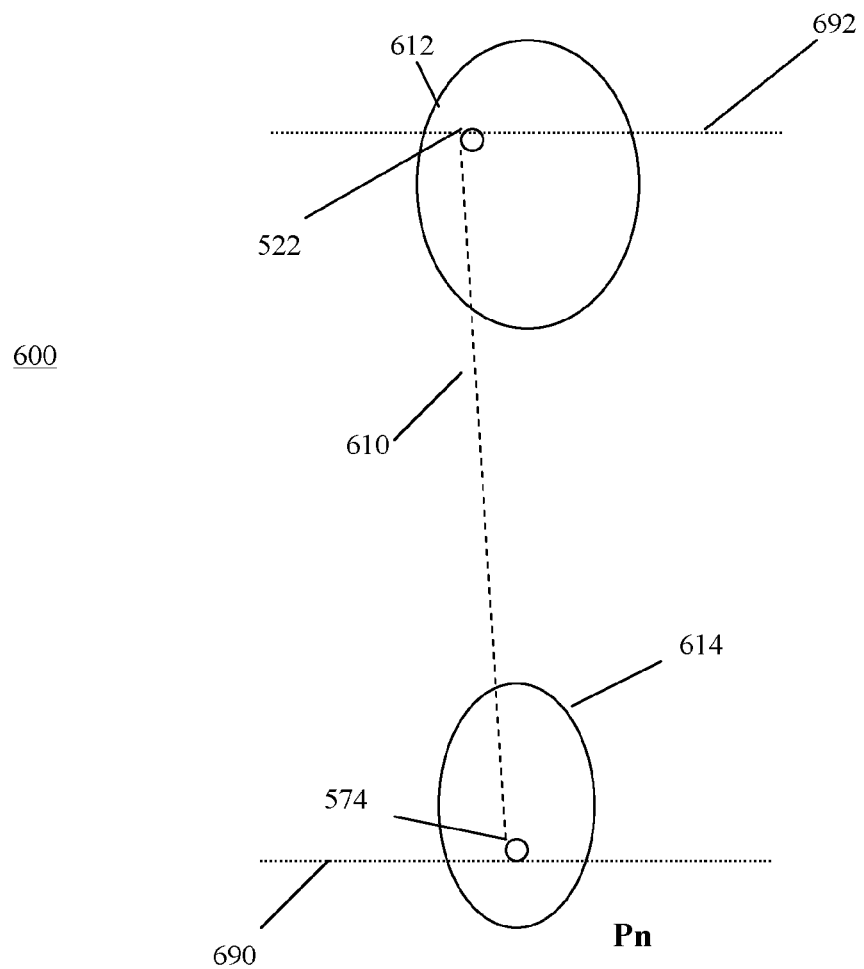
FIG. 6 shows a plan view of a new plane and optimised measurement tool, subsequent to FIG. 5.

FIG. 6 shows a new plane Pn. Plane Pn has been generated from data in the medical image, but does not lie in a plane parallel to any of the slices shown in FIG. 5. Pn contains both points 522 and 574, from FIG. 5. These points have been reproduced on FIG. 6, with the same numbering.

The relationship between the plane Pn in FIG. 6 and planes P and P+1 in FIG. 5 can best be understood by considering lines 690 and 692 in FIG. 6. Line 690 shows the line at which plane Pn would intersect plane P+1 in FIG. 5. Line 692 shows the line at which plane Pn would intersect plane P in FIG. 5

Measurement tool 610 has been drawn on plane Pn. Measurement tool 610 is longer than either of measurement tools 540 and 570 shown in FIG. 5. Thus the length of the measurement tool has been optimised. The display provided to the user can be changed to display the plane Pn in which the optimum measurement lies.

Figure 7:
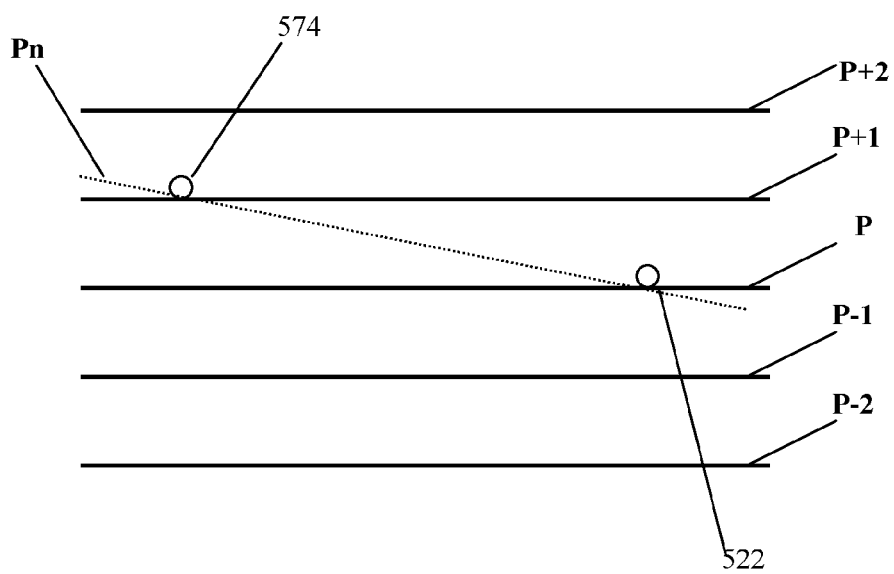
FIG. 7 shows an expanded side elevation view of the planes shown in FIGS. 5 and 6.

FIG. 7 shows an expanded side elevation view of the planes shown in FIGS. 5 and 6.

Plane P in the centre of FIG. 7 is the plane of the image slice that is initially displayed to the user, as explained in connection with FIG. 5. Planes P+2, P+1, P-1, P-2, represent slices of the image that are not displayed to the user, but which are included in the image data available to the system of the invention. After the system locates optimum points 522 and 574, as shown in FIGS. 5 and 6, a new slice of the image represented by plane Pn may be displayed to the user. The measurement tool 610 shown on FIG. 6 lies in plane Pn, and connects points 522 and 574.

Plane Pn intersects only plane P+1 and plane P, in the exploded side elevation view of FIG. 7. In reality, plane Pn may intersect many of the original image slices, since the data points in the image data may lie very close together. In one example, successive slices of a medical image may be separated by 7 mm. Each image slice may comprise a grid of data points, with successive data points across the plane separated by 1 mm in the x- and y-directions.

Region 250 in FIG. 2, and the various regions in FIGS. 4-6 have been shown as ovals, with their long axis aligned with measurement tool 220. However, other forms of region may be used. In general terms, the shape and size of region may be selected to ensure that the search by the automated point detection function occurs in an area or volume that does not extend very significantly away from the direction along which the measurement tool lies.

Considering the 3-d search of FIGS. 5 and 6, it is also clear that each region may be made three dimensional using various approaches. If region 250 in FIG. 2 had been a rectangle, for example, the rectangle could be either:

(i) Rotated about the axis of the measurement tool, to produce a cylindrical search region. The volume of the cylindrical search region would only depend on the length of the sides of the original rectangle.

(ii) Translated into all the image slices in which it was desired to search, in which case the search volume would be a rhomboid.

The assessment of object edge likelihood within a 2-d or a 3-d region may be weighted. With such a weighting, portions of the region nearer to the end of the measurement tool may be assigned higher likelihood than those further away.

The assessment of object edge likelihood may be achieved in a variety of ways. These may include the following list, but other assessment methodologies are also possible. The assessment techniques listed below may be used alone, or in combination:

a) Estimation of the local edge strength by local image derivatives.

b) Estimation of the local edge strength using image-phase based edge detection methods.

c) Estimation of the internal and external image statistics of a feature of interest. This may be based on the initial placement of the measurement tool, and be followed by estimation of the edge strength calculated from the likelihood of belonging to each region.

d) Estimation of the local edge strength based on analysis of training data using supervised or unsupervised learning algorithms.

e) Estimation of the local edge strength from prior knowledge. Such estimation may employ edge definitions as specified by an expert.

The size of the region may be adjusted in a variety of ways. The adjustment may be based on the expected error or accuracy of the location of the end of the measurement tool. The adjustment of each region may depend on at least one of:

a) An amount of image zoom, whereby the accuracy of the location of the end of the measurement tool is assumed to be higher, the more the medical image has been zoomed in. In an alternative, it may be advantageous to assume that the accuracy of the location of the end of the measurement tool is higher, the more the medical image has been zoomed out.

b) An initial length of the measurement tool, whereby the accuracy of the location of the end of the measurement tool is assumed to be higher, the shorter the initial length.

The method of the invention may involve calculating the initial direction of the measurement tool within the plane of a medical image. Points such as points 330 and 340 in FIG. 3, or 424 and 432 in FIG. 4, may then be selected to have a predetermined relationship with the original direction of the measurement tool. For example, they may be selected in consideration of the angle between the initial placement of the measurement tool and its orientation when connected to the selected points. That angle may be kept below a certain limit.

The assessment of object edge likelihood can be filtered or weighted to take account of prior expectation or knowledge. For example, the assessment of object edge likelihood may be filtered or weighted on the basis of the direction of the measurement tool, so that edges lying normal to the direction of measurement tool are considered of higher likelihood than those parallel to the direction of measurement tool.

When the direction of the measurement tool has been determined, the size or shape of a basic initial search region may be adjusted to be larger in a direction parallel to the measurement tool than in a direction perpendicular to the measurement tool. This has been done with region 250 shown in FIG. 2.

When the point detection function is applied to both ends of a measurement tool, and a sub-set of candidate features is found for each end, then potential features may be evaluated simultaneously in the two regions. This joint selection of points can be controlled in such a way that it optimises the output of the measurement tool.

The method of the invention may be used to calculate parameters from scan data in various situations. In particular, the method of the invention may be used with, or in, any of the following:
(i) Picture archiving and communication systems (PACS).
(ii) Radiological information systems (RIS).
(iii) Hospital information systems (HIS).
(iv) Advanced visualisation workstations.
(v) Imaging Acquisition Workstations.
(vi) Web based or cloud based medical information and image systems.

Figure 8:
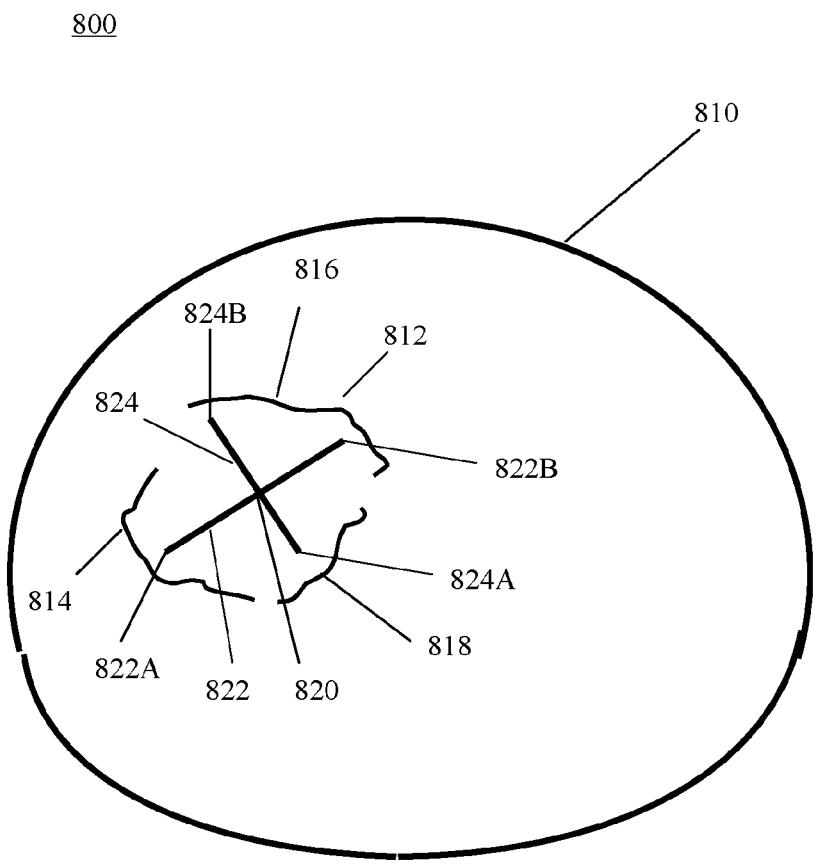
FIG. 8 shows a bidirectional measurement tool in accordance with an embodiment of the invention.

FIG. 8 shows a medical image 800. Perimeter 810, and the first part 814 and third part 818 of structure 812 on FIG. 8 generally correspond to the similarly numbered features on medical images 200 and 300 shown on FIGS. 2 and 3. Second part 816 of structure 812 on FIG. 8 is more extensive than the second parts 216 and 316 shown on FIGS. 2 and 3.

Measurement tool 820 on FIG. 8 is 'bidirectional'. Bidirectional measurement tool 820 comprises a first section 822 and a second section 824. First section 822 and second section 824:
(i) Cross each other.
(ii) Comprise straight lines, held perpendicular to each other.
(iii) Are moveable, relative to each other.
First section 822 has a first end 822A and a second end 822B. Second section 824 has a third end 824A and a fourth end 824B.

Figure 9:
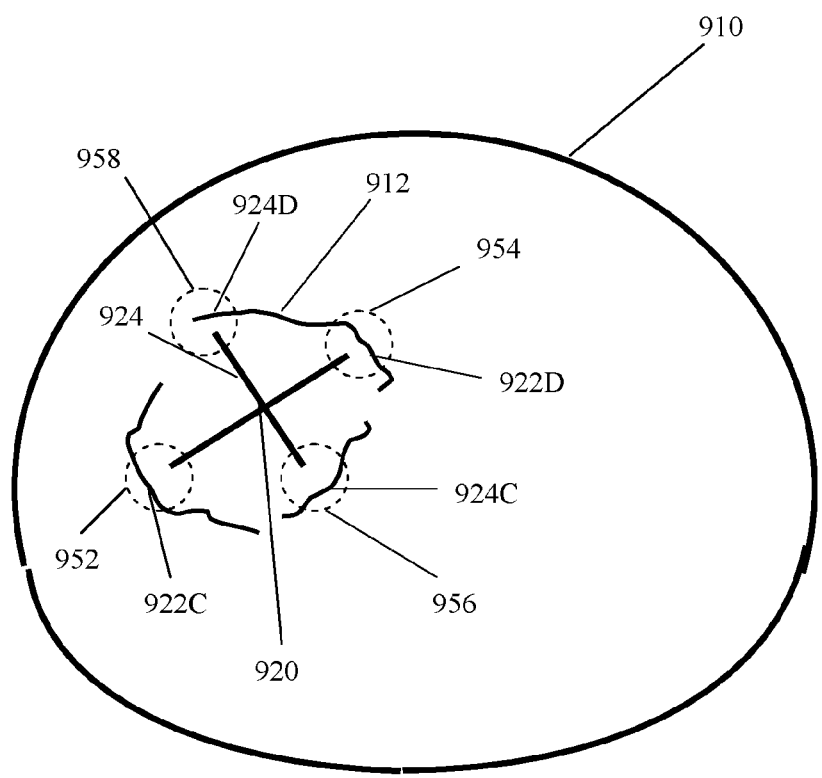
FIG. 9 shows a subsequent view of the bidirectional measurement tool of FIG. 8.

FIG. 9 corresponds to FIG. 8. However the three parts of the structure 812 shown on FIG. 8 have had their reference signs and labels omitted from structure 912 in FIG. 9, in order to simplify the figure. Similarly, first section 822 and second section 824 of bidirectional measurement tool 820 shown on FIG. 8, and the four ends of the measurement tool, have not been labelled on bidirectional measurement tool 820 in FIG. 9.

FIG. 9 shows first region 952, second region 954, third region 956 and fourth region 958. Each of these regions is circular, and encompasses one of the ends of the bidirectional measurement tool 920. Each of regions 952, 954, 956 and 958 defines a portion of the medical image in which a search is made by a point detection function.

The point detection function has identified four points, one in each of the four regions 952, 954, 956 and 958. Each point is labelled 922C, 922D, 924C and 924D.

The ends of the bidirectional measurement tool 920 have not moved or 'snapped' to the points 922C, 922D, 924C and 924D identified in each of regions 952, 954, 956 and 958. However, this may occur. Whether or not such movement occurs, the method of the invention may use any or all of points 922C, 922D, 924C and 924D in performing a measurement of a parameter of structure 912.

The method of the invention as applied in FIG. 9 may select potential edge locations by filtering the edge likelihood, to give binary edge/not edge detection. This filtering can be performed by applying a threshold to the likelihood, for example. The method comprises a search of all nearby edge locations in the or each region, to optimise the measurement as required. For example, for the long axis, the system would find the pair of edge points that gives the longest in plane measurement. The system may then move the ends of the measurement tool to the optimal locations.

The bidirectional measurement tool shown in FIGS. 8 and 9 may be particularly useful for obtaining measurements of the long axis and the short axis of a structure, such as a tumour. These measurements can then be used in the WHO/RECIST techniques described in the Background section above.

Figure 10:
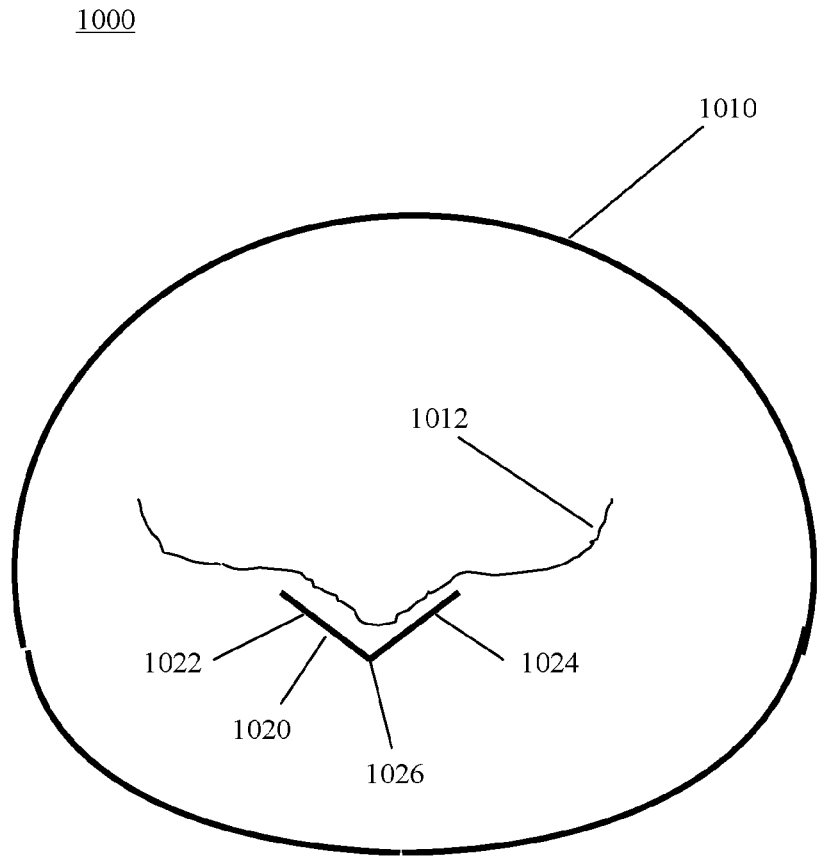
FIG. 10 shows a protractor in accordance with an embodiment of the invention.

In an alternative embodiment of the invention, illustrated generally in FIG. 10, the measurement tool may be a protractor. The protractor may comprise two measurement arms connected at a hinge, the two arms lying at an angle to each other. The angle swept out by the hinge varies.

FIG. 10 shows a medical image 1000. Within the perimeter 1010 is a structure 1012. Structure 1012 is an anatomical feature within the medical image. The lower, central portion of structure 1012 has a generally V-shape.

Protractor 1020 is arranged adjacent to the central portion of structure 1012. Protractor 1020 has a first measurement arm 1022 and a second measurement arm 1024, which are joined at hinge 1026. The initial alignment of first measurement arm 1022 and second measurement arm 1024 may be chosen by a user.

In accordance with this embodiment of the invention, an automated point detection function is applied to at least one region of medical image 1010. Each region comprises the end of one of the measurement arms. The automated point detection function may comprise an assessment of object edge likelihood.

The assessment of object edge likelihood may be filtered or weighted on the basis of the direction of the corresponding measurement arm of protractor tool 1020. The region may be shaped, on the basis of the direction of the measurement arm. Such shaping, filtering or weighting, therefore, can include the following more detailed options:
(i) Object edges lying parallel to the direction of the at least one arm may be considered to be of higher likelihood than those perpendicular to the direction of the arm, using weighting or filtering to achieve this.
(ii) The shape of at least one region around the location of the end of at least one arm may be adjusted in dependence on the initial direction of the arm, whereby the region is larger in a direction perpendicular to the arm.

In addition, the hinge 1026 of protractor 1020 may move either to:
(i) A point identified as having high edge likelihood; or
(ii) A point determined by the local image edge orientation adjacent to at least one of the two measurement arms.

Figure 11:
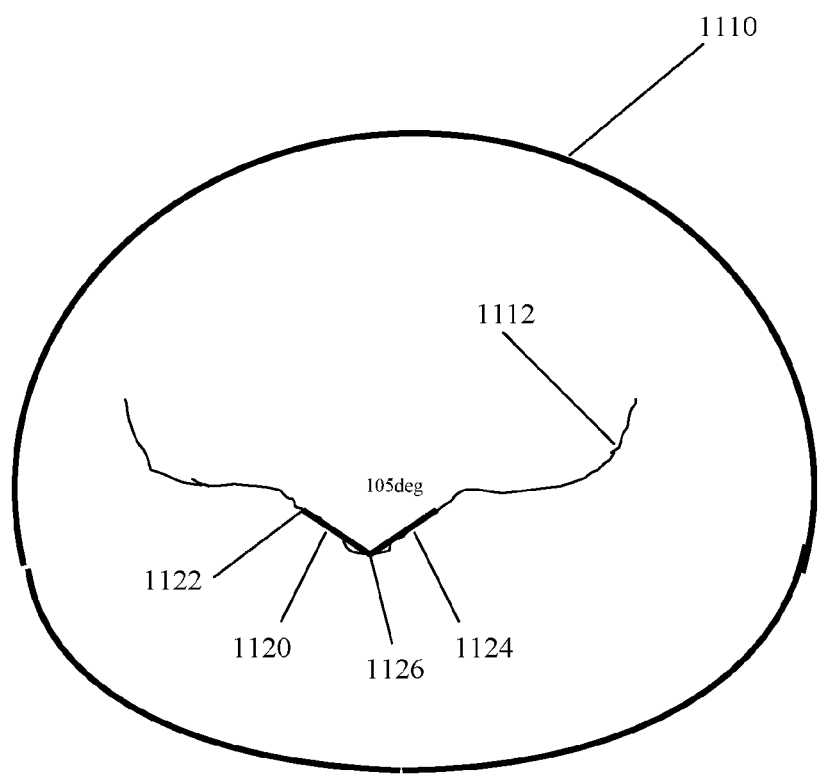
FIG. 11 shows a subsequent view of the protractor of FIG. 10.

FIG. 11 shows a further view of the measurement tool of FIG. 10.

Medical image 1100 comprises perimeter 1110 and structure 1112. After application of the point detection function, the first measurement arm 1122 and the second measurement arm 1124 of protractor 1120 have moved or snapped to orientations that lie parallel to portions of the structure 1112. The angle between the first and second measurement arms may be displayed on the screen in the vicinity of the protractor. Entirely as an illustrative numerical example, an angle of 105 degrees is shown on FIG. 11.

The embodiments of FIGS. 2-3 and 8-11 show the application of the method of the invention to a single slice from the medical image, i.e. from the data obtained in a medical scan. FIGS. 4-7 show the application of the method of the invention to a region that spans multiple slices from the medical image. However, data may be obtained:

(i) As multiple images obtained at the same time, for example on the same day. These may be obtained with different machines, or with different settings on one machine.

(ii) As multiple images obtained at different times, for example over a period of days, weeks or years. Such images may provide multiple versions of the same slice(s) separated in time. The medical scan might, for example, have been performed on the head or torso of a person. There might be images of the same head or torso, which were taken over a period of days, weeks or longer.

In addition to the examples given in FIGS. 2-11, therefore, the method of the invention may be applied to multiple medical images that have been obtained at different times, or on one occasion by multiple machines or with multiple settings on one machine.

When applied to multiple slices of medical scan image data, either from one scan or from different scans performed at different times, the method of the invention may further comprise:

(i) Displaying at least two measurement tools, either on one displayed slice, or on multiple slices taken at different times.
(ii) Linking together the at least two measurement tools.
(iii) Imposing an additional constraint on the measurement tools, the additional constraint serving to apply an additional limitation on the points that can be selected by the point detection function.

Considering (iii) further, there may be multiple measurements, when there are either multiple images in a series, or multiple measurement tools within a single image. In these situations, additional measurement constraints may be imposed. For example, there may be a constraint that:

(i) Rulers must have the same orientation within the image plane or the displayed images; or
(ii) For multiple images in a series, the ruler measurements should be taken on image planes having the same orientation for each image in a series. In such cases, the user would indicate which rulers should be linked, and thus have the constraint applied to them. The method could involve automatically applying a constraint, or the user could specify which constraint should be applied to the measurement.

The method of the invention would apply the constraint in the following manner:

(i) For constraints that have an optimal solution, e.g. rulers should have the same orientation, the selected points, i.e. the control point positions for all linked measurement tools, would be chosen according to the search methods described above. However, the optimisation would take account of the additional optimisation criteria.
(ii) The invention may provide a notification to a user when the additional constraint cannot be applied to at least one of the linked measurement tools. This might occur for constraints that cannot be sensibly optimised. For example, the constraint could be a condition that rulers should be drawn on image planes having the same orientation. This is only possible if the image slices that are available meet this criterion, and none were taken in a different orientation. If one or more of the slices did not have the required orientation, then deviations from the constraint would be detected, based either on the approximate measurement tools or on the individually optimised measurement tools. In addition, the user's initial selection of approximate control points may exclude optimisation, i.e. it is not possible to carry out the optimisation, from where the user started. Once notified of the problem, the user could then adjust the measurement tool or tools as needed, until the constraint is met, or the constraint could be automatically optimised.

With each embodiment of the invention described above, particularly in connection with FIGS. 2-11, a user may inspect the result and adjust if necessary. So the points identified by the point detection function may be altered or over-ridden by a user. In addition, when weighting or filtering is used, the user may adjust the weighting or filtering and then re-apply the method using the revised weighting or filtering criteria. Hence the method of the present invention may be applied iteratively.

FIGS. 12-15 show various different examples of 2-d local search area adaption, weighting and filtering in accordance with embodiments of the invention. Corresponding 3-d versions of the search area adaptation also apply.

Figure 12A:
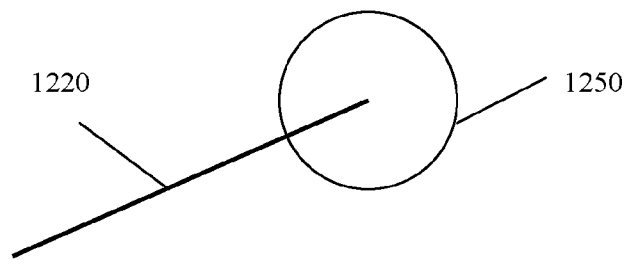
FIGS. 12-15 show examples of local search area adaption, weighting and filtering in accordance with various embodiments of the invention.

FIG. 12*a* shows a portion of a measurement tool 1220. Reference 1250 indicates a uniform region, of circular shape, which constitutes the search area for the object recognition function of the invention in this embodiment.

Figure 12B:
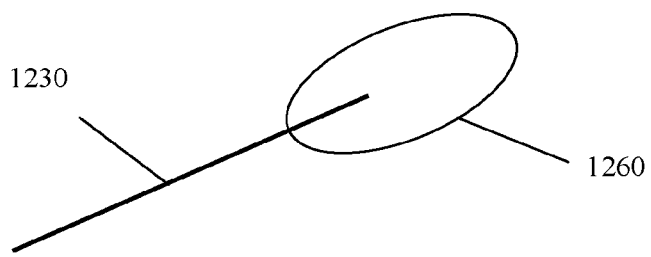

FIG. 12*b* shows a portion of a measurement tool 1230. Reference 1260 indicates the region that constitutes the search area for the object recognition function of the invention in this embodiment. Region 1260 is shaped according to the direction of the measurement tool 1230, but is uniform, so is not weighted or filtered.

Figure 13A:
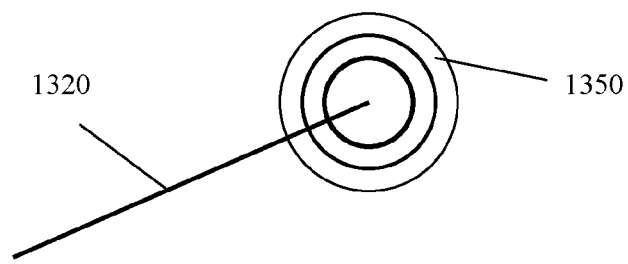

FIG. 13*a* shows a portion of a measurement tool 1320. Reference 1350 indicates a distance weighted region, which constitutes the search area for the object recognition function of the invention in this embodiment. Within distance weighted region 1350, concentric rings with successively thinner lines are shown to illustrate successively lower weightings.

Figure 13B:
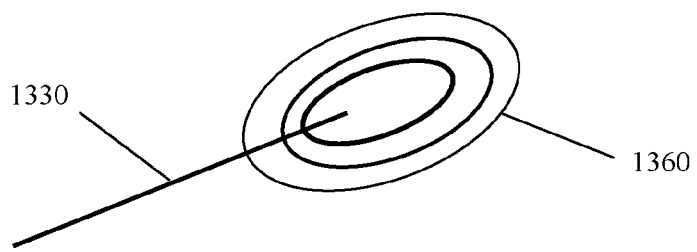

FIG. 13*b* shows an adaption of FIG. 13*a*. A portion of a measurement tool 1330 is shown on FIG. 13*b*. Reference 1360 indicates a region weighted both by distance from the end of the measurement tool, and shaped and weighted according to the direction of the measurement tool 1330. Hence region 1360 is both weighted and shaped. Region 1360 constitutes the search area for the object recognition function of the invention in this embodiment. Within region 1360, concentric ovals with successively thinner lines are shown to illustrate successively lower weightings.

Figure 14A:
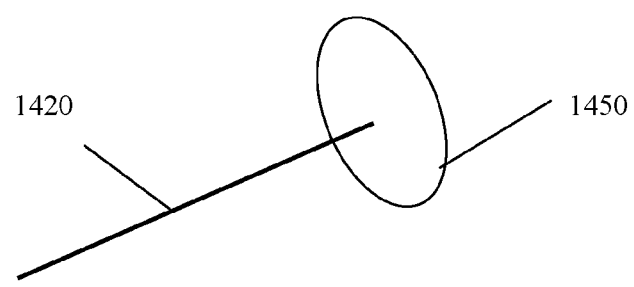

FIG. 14*a* shows a portion of a measurement arm 1420 of a protractor tool. Reference 1450 constitutes the search area for the object recognition function of the invention in this embodiment. Region 1450 is a uniform search area, whose shape is elongated in a direction perpendicular to the direction of protractor measurement arm 1420.

Figure 14B:
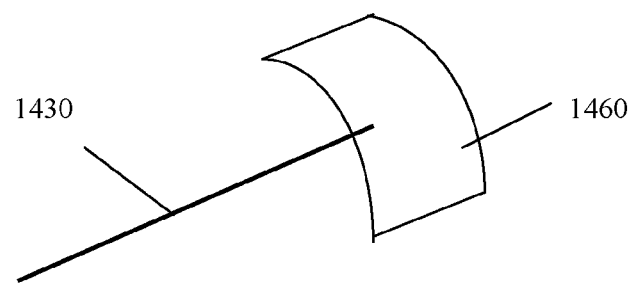

FIG. 14*b* shows a portion of a measurement arm 1430 of a protractor tool. Reference 1460 constitutes the search area for the object recognition function of the invention in this embodiment. Region 1460 is a uniform search area. The shape of search area 1460 is determined by the protractor hinge location and the length or radius of the measurement arm 1430.

Figure 15A:
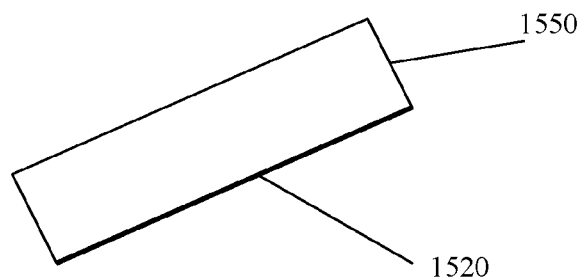

FIG. 15*a* shows a portion of a measurement arm 1520 of a protractor tool. Reference 1550 constitutes the search area for the object recognition function of the invention in this embodiment. Region 1550 is a uniform search area. The shape of search area 1550 is generally rectangular, and search area lies along one side of measurement arm 1520.

Figure 15B:
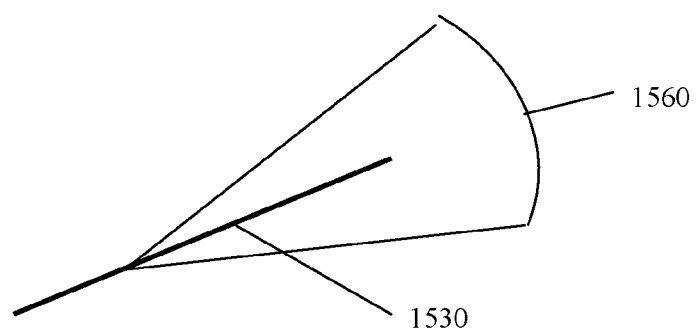

FIG. 15*b* shows a portion of a measurement arm 1530 of a protractor tool. Reference 1560 constitutes the search area for the object recognition function of the invention in this embodiment. Region 1560 is a uniform search area. The search area provided by region 1560 is generally fan shaped. Region 1560 may taper back to any point along the measurement arm, and may lie on both sides or on one side of measurement arm 1530.

Figure 16:
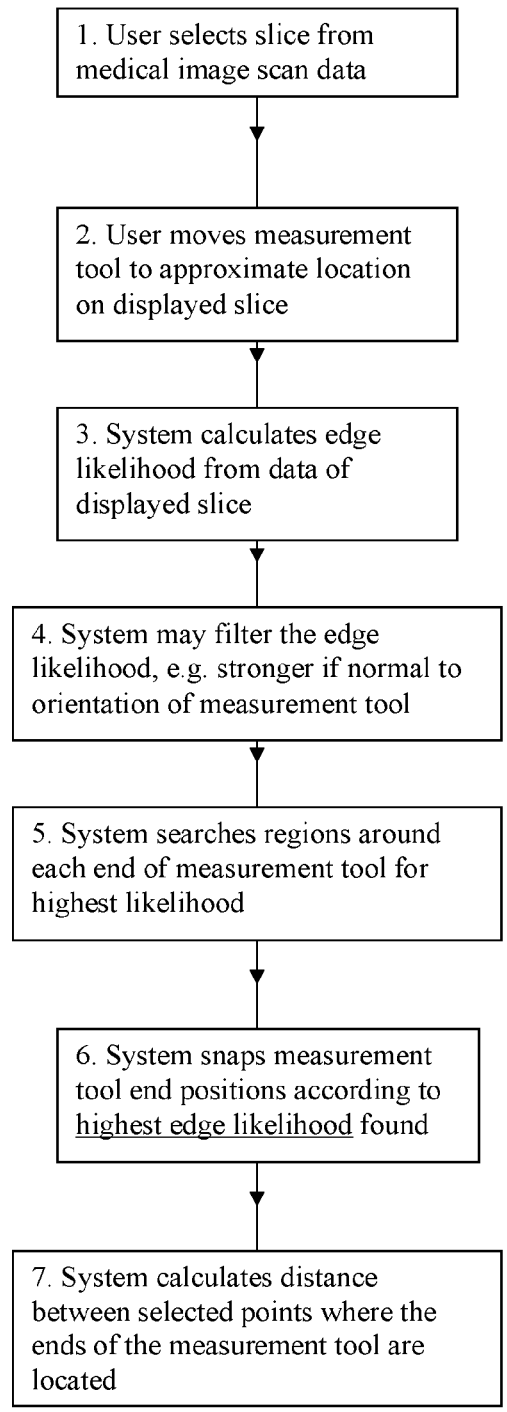
FIG. 16 is a flow chart showing a detailed example of the method that may be used with measurement tools of the forms generally illustrated in FIGS. 2-9.

FIG. 16 is a flow chart showing a detailed example of a method that may be used with measurement tools of the forms generally illustrated in FIGS. 2-9. Each of steps 1-6 of the flowchart of FIG. 16 occurs in sequence.

The example illustrated in FIG. 16 involves the calculation of object edge likelihood within each of two regions, see step 3. The selected points in each region are those with highest likelihood, see step 5. Step 5 may optionally comprise weighting, e.g. by distance from and/or orientation of, each portion of the region, relative to the location where the ends of the measurement tool were initially placed.

Figure 17:
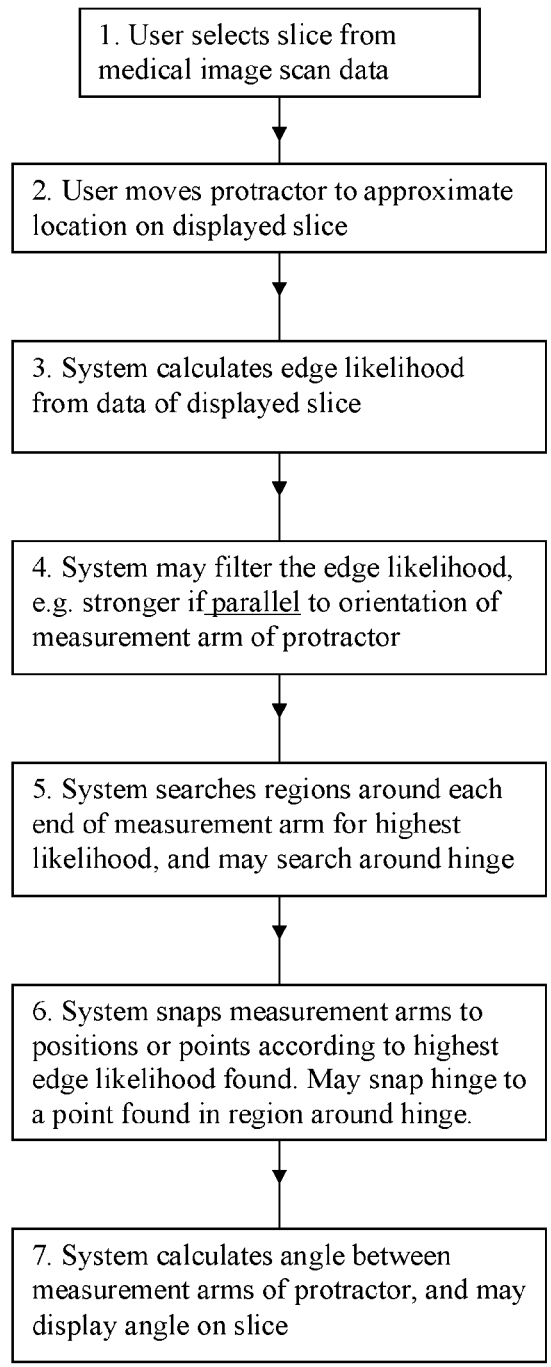
FIG. 17 is a flow chart showing a detailed example of the method that may be used with measurement tools in the form of the protractor generally illustrated in FIGS. 10 and 11.

FIG. 17 is a flow chart showing a detailed example of the method that may be used with the protractor generally illustrated in FIGS. 10 and 11. The example illustrated in FIG. 17 involves the calculation of object edge likelihood within each of two regions and in addition at the hinge point of the protractor.

Each of steps 1-7 of the flowchart of FIG. 17 occurs in sequence. Step 4 may optionally comprise weighting, e.g. by distance from, and/or orientation of, each portion of the region, relative to the location where the ends or measurement arms of the protractor were initially placed. This weighting may also involve the direction of the measurement arm. In step 6, the position of the hinge may be adjusted according to the local image orientation that has been found, i.e. in accordance with the final directions of the measurement arms.

Figure 18:
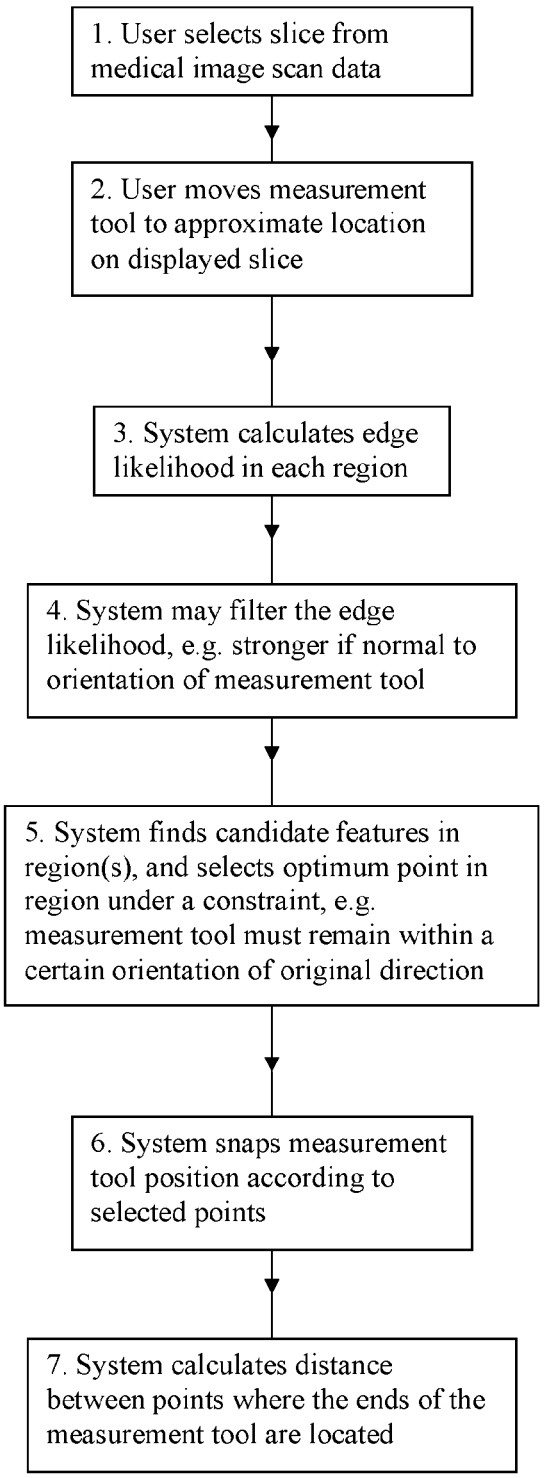
FIG. 18 is a flow chart showing a detailed example of the method of the invention when a constraint is in force.

FIG. 18 is a flow chart showing a detailed example of the method of the invention when a constraint is in force. In the method of FIG. 18, the edge likelihoods are converted into probable edges, to provide the sub-set of candidate features. See in particular step 5 of FIG. 18.

Figure 19:
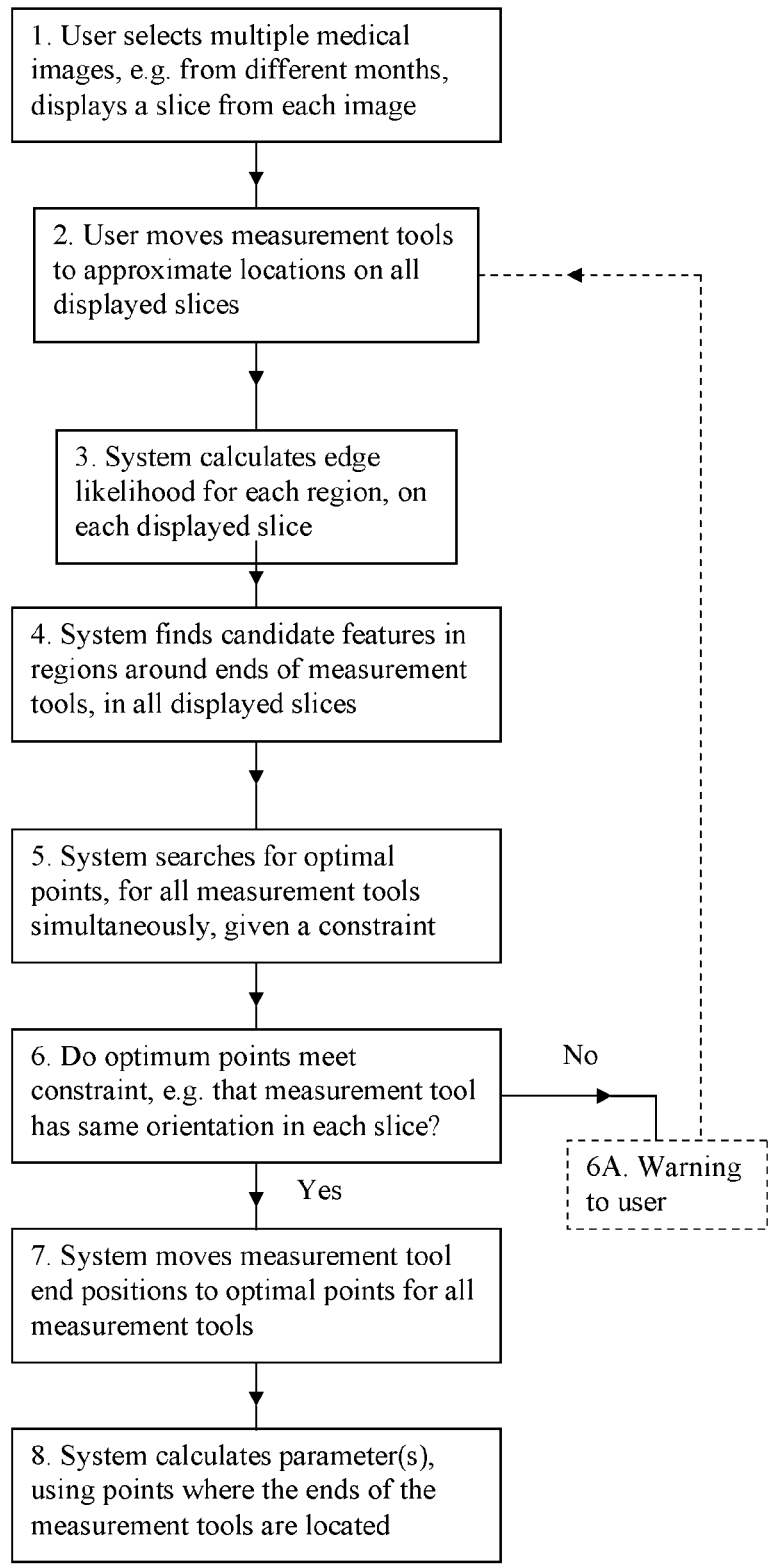
FIG. 19 is a flow chart showing a detailed example of the method of the invention applied to multiple images, with a constraint.

FIG. 19 is a flow chart showing a detailed example of the method of the invention applied when a constraint is in force. The method is applied simultaneously to multiple displayed slices, from multiple images. As a variant, the method may be applied to multiple measurement tools displayed on a single image.

Step 8 of FIG. 19 shows a successful outcome. The system is able to calculate one or more parameters. This calculation uses the points for the ends of the measurement tools that are derived in steps 6 and 7.

In some situations, the outcome of the method of the flowchart of FIG. 19 will be different, i.e. it will not reach step 8 at a first run through. In some situations, the constraint applied to multiple images cannot be met by optimisation. In these situations, step 6 results in a warning message to the user. This is shown in step 6A.

An example of a situation where the constraint cannot be met by optimisation would be when the constraint is that all measurement tools should be drawn on one plane, e.g. the axial plane, but at least one of the image slices is not orientated in that plane. Such a limitation to the axial plane might, for example, arise when making the RECIST or WHO measurements described in the Background section above.

If a measurement constraint is violated, and an optimisation is not possible, then the user may intervene in response to the warning. For example, the user might alter the constraint, or one or more images may be removed from the set of images. The user may return to step 2.

In a further embodiment, the invention comprises a computer program, comprising computer-executable code. When executed on a computer system, the computer-executable code causes the computer system to perform a method according to any of the preceding embodiments of the invention. In a further embodiment of the invention, a computer-readable medium is provided, storing such a computer program.

Figure 20:
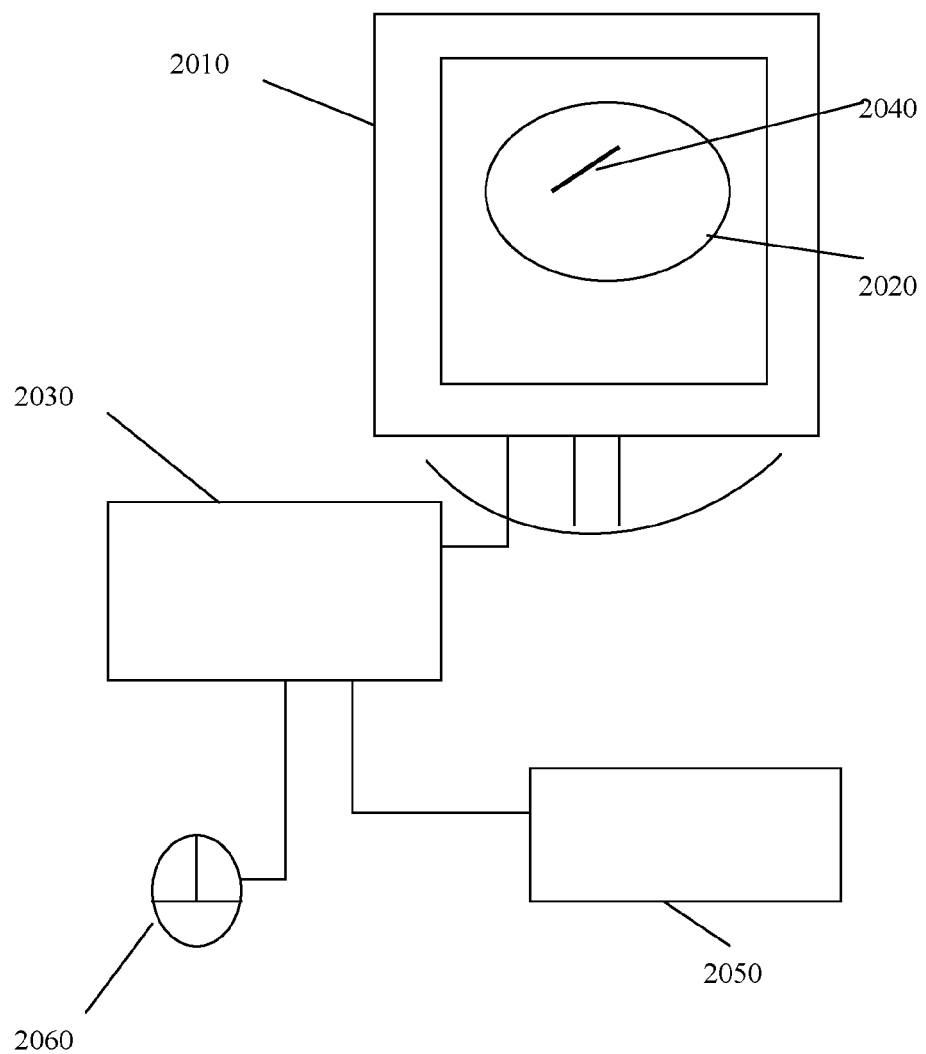
FIG. 20 shows an embodiment of a system in accordance with the invention.

FIG. 20 shows an embodiment of a system 2000 in accordance with the invention. System 2000 of FIG. 20 enables the measurement of a parameter of a structure on a medical image.

The system comprises a display 2010, for displaying a soft copy of a medical image 2020.

A module 2030 is capable of displaying, and or adapted to display, a measurement tool 2040 on the medical image 2020. Measurement tool 2040 comprises at least two ends.

A user interface may comprise a keyboard 2050 and a mouse 2060. The user interface may in addition, or instead, comprise a touch-sensitive input screen.

The user interface 2050, 2060 allows a user to place each of the at least two ends of measurement tool 2040 in proximity to a corresponding feature of interest on the medical image 2020. The features of interest form part of the structure. Features of interest forming a structure are shown, for example, in FIGS. 2-11.

Module 2030 is further capable of, and/or adapted to:
(i) Apply an automated point detection function to at least one region of the medical image 2020, each region comprising one of the ends of measurement tool 2040. Examples of such regions are shown on FIGS. 2, 9 and 12-15. The automated point detection function is capable of identifying, and or adapted to identify, a selected point within the region that optimises the placement of the respective end of the measurement tool. The selected point may be the point within the one region having the highest likelihood of being the corresponding feature of interest. The selected point may however be selected from a sub-set of candidate features, identified within the region, the selected point optimising the measurement from amongst the candidate features.
(ii) Performing a measurement of a parameter of the structure, using the point or points identified by the automated point detection function.

The system of FIG. 20 may be implemented in a workstation. Such a workstation may be capable of implementing any of the methods described above.

The invention claimed is:

1. A method of measuring a parameter of a structure on a medical image, comprising:
   displaying a slice of a medical image;
   displaying a measurement tool on the slice of the medical image, the measurement tool comprising at least two ends, each end of the measurement tool being placed at a location within the medical image in proximity to a corresponding feature of interest, the features of interest forming part of the structure;
   determining at least one region of the medical image comprising the location within the medical image at which one of the ends of the measurement tool has been placed;
   applying an automated point detection function to the at least one region of the medical image; wherein the step of applying the automated point detection function comprises:
      filtering potential features within the at least one region to provide a sub-set of candidate features of interest within the at least one region;

identifying a candidate feature in the at least one region that adheres to one or more constraints on the orientation of the measurement tool and maximizes the length of the measurement tool; and using the identified candidate feature as a selected point within the at least one region that optimizes the placement of the respective end of the measurement tool; and performing a measurement of a parameter of the structure using the selected point or points identified by the automated point detection function.

2. The method in accordance with claim 1, wherein:

the at least one region comprises a two dimensional area of the displayed slice of the medical image; and for the at least one region, the automated point detection function identifies a selected point within the displayed slice of the medical image that optimizes the placement of the respective end of the measurement tool;

whereby, in the optimized placement, the ends of the measurement tool lie within the plane of the displayed slice of the medical image.

3. The method in accordance with claim 1, further comprising the step of:

moving at least one end of the measurement tool to the selected point on the displayed slice of the medical image.

4. The method in accordance with claim 1, wherein:

the at least one region comprises a 3-dimensional volume of the medical image, the at least one region comprising part of the displayed slice of the medical image and part of at least one other slice of the medical image; and for the at least one region, the automated point detection function identifies a selected point within one of the image slices that optimizes the placement of the respective end of the measurement tool;

whereby, in the optimized placement, one or more ends of the measurement tool may lie within other slices of the medical image than the displayed slice.

5. The method in accordance with claim 4, further comprising the step of:

moving at least one end of the measurement tool to the selected point; and if at least one end of the measurement tool does not lie within the displayed slice, displaying a new slice of the medical image, the new slice comprising the ends of the measurement tool, whereby the new slice may not be parallel to the originally displayed slice.

6. The method in accordance with claim 1, wherein the step of applying the automated point detection function further comprises the step of:

finding a point within the region having a highest likelihood of being the feature of interest, and selecting the point having the highest likelihood of being the feature of interest as the selected point.

7. The method in accordance with claim 1, wherein:

the feature of interest is a feature at which a rate of intensity variation is greatest.

8. The method in accordance with claim 1, wherein:

the step of filtering the potential features to provide the sub-set of candidate features of interest within the region comprises comparing at least one of the following values for each potential feature against a minimum threshold value:

(i) feature strength;
(ii) edge likelihood;
(iii) probability.

9. The method in accordance with claim 1, wherein applying the automated point detection function further comprises the step of:

simultaneously evaluating potential features in at least two regions; and identifying the selected point in each region so as to jointly optimize the output of the measurement tool.

10. The method in accordance with claim 9, wherein the measurement tool is bidirectional, comprising a first section and a second section, wherein the first section and the second section:

(i) cross each other;
(ii) comprise straight lines, held perpendicular to each other;
(iii) are moveable, relative to each other; and the first section has a first end and a second end, and the second section has a third end and a fourth end.

11. The method in accordance with claim 1, wherein applying the automated point detection function further comprises the step of:

assessing object edge likelihood for points within the at least one region, and identifying potential features within the at least one region based on the assessment of object edge likelihood.

12. The method in accordance with claim 11, wherein:

the selected point for the region is a potential feature that has a highest object edge likelihood within said region.

13. The method in accordance with claim 11, further comprising:

calculating the direction of the measurement tool within the plane of the medical image; and wherein: each selected point has a predetermined relationship with the direction of the measurement tool.

14. The method in accordance with claim 13, further comprising the steps of:

assessing object edge likelihood;

filtering or weighting the assessment of object edge likelihood on the basis of the direction of the measurement tool, whereby edges lying normal to the direction of the measurement tool are considered of higher likelihood than those parallel to the direction of the measurement tool; and identifying potential features within said region based on the assessment of object edge likelihood.

15. The method in accordance with claim 13, wherein:

the size or shape of the at least one region is adjusted to be larger in a direction parallel to the measurement tool than in a direction perpendicular to the measurement tool.

16. The method in accordance with claim 1, wherein the assessment of object edge likelihood comprises estimation of at least one of the following:

a) the local edge strength, using local image derivatives;
b) the local edge strength, using image-phase based edge detection methods;
c) the internal and external image statistics of a feature of interest, followed by estimation of the edge strength calculated from the likelihood of belonging to each region;
d) the local edge strength, based on analysis of training data using supervised or unsupervised learning algorithms;
e) the local edge strength, from prior knowledge.

17. The method in accordance with claim 1, wherein applying the automated point detection function further comprises the step of:

weighting each potential feature or each candidate feature within the sub-set of candidate features, within said region, in dependence on the position of the feature within the region, whereby features nearer the end of the measurement tool are assigned higher weighting than those further away.

18. The method in accordance with claim 1, wherein the size of the at least one region is adjusted in dependence on an expected accuracy of the location of the end of the measurement tool within the at least one region, the adjustment depending on at least one of:
   a) an amount of image zoom, whereby the accuracy of the location of the end of the measurement tool is assumed to be higher, the more the medical image has been zoomed in;
   b) an initial length of the measurement tool, whereby the accuracy of the location of the end of the measurement tool is assumed to be higher, the shorter the initial length.

19. The method in accordance with claim 1, wherein:
   (i) the measurement tool is a protractor, the protractor comprising two measurement arms connected at a hinge, the two arms lying at an angle to each other;
   (ii) applying the automated point detection function comprises assessing object edge likelihood;
   (iii) a resulting assessment of object edge likelihood is filtered or weighted on the basis of the direction of at least one arm of the protractor, whereby:
   object edges lying parallel to the direction of the at least one arm are considered to be of higher likelihood than those lying perpendicular to the direction of the arm; and/or
the shape of at least one region around the location of the end of at least one arm is adjusted in dependence on the initial direction of the arm, whereby the region is larger in a direction perpendicular to the arm.

20. The method in accordance with claim 19, the measurement tool being a protractor, the protractor comprising two measurement arms connected at a hinge, and wherein the hinge moves either to:
   (i) a point identified as having high edge likelihood; or (ii) a point determined by the local image edge orientation adjacent to at least one of the two measurement arms.

21. The method in accordance with claim 19, further comprising the steps of:
   (i) displaying at least two measurement tools, either on one medical image, or on multiple medical images, which may be taken at different times;
   (ii) linking together the at least two measurement tools;
   (iii) imposing an additional constraint on the measurement tools, the additional constraint serving to apply an additional limitation on the points that can be selected by the point detection function.

22. The method in accordance with claim 21, further comprising the step of:
   notifying a user when the additional constraint cannot be applied to at least one of the linked measurement tools.

23. A non-transitory computer-executable memory for use in a computer system, the memory have stored therein executable code for performing the method steps according to claim 1.

24. A system for measuring a parameter of a structure on a medical image, comprising:
   a display, for displaying a soft copy of a medical image;
   a module capable of generating a measurement tool for displaying on the medical image, the measurement tool comprising at least two ends;
   a user interface, the user interface allowing a user to place each of the at least two ends of the measurement tool in proximity to a corresponding feature of interest on the medical image, the features of interest forming part of the structure;
   the module being further capable of:
   (i) determining at least one region of the medical image comprising the location within the medical image at which one of the ends of the measurement tool has been placed;
   (ii) applying an automated point detection function to the at least one region of the medical image, the automated point detection function:
      filtering potential features within the at least one region to provide a sub-set of candidate features of interest within the at least one region;
      identifying a candidate feature in the at least one region that adheres to one or more constraints on the orientation of the measurement tool and maximizes the output of the measurement tool; and
      using the identified candidate feature as a selected point within the at least one region that optimizes the placement of the respective end of the measurement tool; and
   (iii) performing a measurement of a parameter of the structure, using the point or points identified by the automated point detection function.

25. The system as claimed in claim 24, wherein the system is a medical imaging workstation.

26. The system as in claim 24, further comprising a computer-executable code stored on a non-transitory computer readable medium for execution by the module.

27. A method of measuring a parameter of a structure on a medical image, comprising:
   displaying a slice of a medical image;
   displaying a measurement tool on the slice of the medical image, the measurement tool comprising at least two ends, each end of the measurement tool being placed at a location within the medical image in proximity to a corresponding feature of interest, the features of interest forming part of the structure;
   determining at least one region of the medical image comprising the location within the medical image at which one of the ends of the measurement tool has been placed;
   applying an automated point detection function to the at least one region of the medical image;
   the automated point detection function identifying a selected point within the at least one region that optimizes the placement of the respective end of the measurement tool; and
   performing a measurement of a parameter of the structure using the selected point or points identified by the automated point detection function,
wherein:
   the at least one region comprises a 3-dimensional volume of the medical image, the at least one region comprising part of the displayed slice of the medical image and part of at least one other slice of the medical image; and
   for the at least one region, the automated point detection function identifies a selected point within one of the image slices that optimizes the placement of the respective end of the measurement tool;
   whereby, in the optimized placement, one or more ends of the measurement tool may lie within other slices of the medical image than the displayed slice.

* * * * *